(12) United States Patent
Saha et al.

(10) Patent No.: US 11,202,599 B2
(45) Date of Patent: Dec. 21, 2021

(54) SYSTEMS AND METHODS FOR DETECTING ARRHYTHMIAS

(71) Applicant: Cardiac Pacemakers, Inc., St. Paul, MN (US)

(72) Inventors: Sunipa Saha, Shoreview, MN (US); David L. Perschbacher, Coon Rapids, MN (US); Deepa Mahajan, North Oaks, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 176 days.

(21) Appl. No.: 16/388,233

(22) Filed: Apr. 18, 2019

(65) Prior Publication Data
US 2019/0343415 A1 Nov. 14, 2019

Related U.S. Application Data

(60) Provisional application No. 62/668,392, filed on May 8, 2018.

(51) Int. Cl.
*A61B 5/0464* (2006.01)
*A61B 5/00* (2006.01)
(Continued)

(52) U.S. Cl.
CPC .............. *A61B 5/363* (2021.01); *A61B 5/352* (2021.01); *A61B 5/7221* (2013.01); *A61B 5/7267* (2013.01)

(58) Field of Classification Search
CPC ... A61B 5/0464; A61B 5/0456; A61B 5/7221; A61B 5/7267
(Continued)

(56) References Cited

U.S. PATENT DOCUMENTS

2005/0043614 A1* 2/2005 Huizenga ............... C23F 11/08
600/427
2007/0149890 A1 6/2007 Li et al.
(Continued)

FOREIGN PATENT DOCUMENTS

CN 112105415 A 12/2020
WO WO-2016118712 A1 7/2016
(Continued)

OTHER PUBLICATIONS

"International Application Serial No. PCT/US2019/028113, International Preliminary Report on Patentability dated Nov. 19, 2020", 7 pgs.
(Continued)

*Primary Examiner* — Erin M Piateski
(74) *Attorney, Agent, or Firm* — Schwegman Lundberg & Woessner, P.A.

(57) ABSTRACT

Systems and methods for ambulatory detection of medical events such as cardiac arrhythmia are described herein. An embodiment of an arrhythmia detection system may include a detection criterion circuit that determines a patient-specific detection criterion using a baseline cardiac characteristic when the patient is free of cardiac arrhythmias. The detection criterion circuit generates a patient-specific threshold of a signal metric by adjusting a population-based threshold of the signal metric, where the manner and the amount of adjustment is based on information about patient baseline cardiac characteristic. The arrhythmia detection system detects an arrhythmia episode using a physiologic signal sensed from the patient and the patient-specific arrhythmia detection threshold.

20 Claims, 8 Drawing Sheets

(51) Int. Cl.
  *A61B 5/0456* (2006.01)
  *A61B 5/363* (2021.01)
  *A61B 5/352* (2021.01)
(58) Field of Classification Search
  USPC .......................................................... 600/518
  See application file for complete search history.

(56) References Cited

U.S. PATENT DOCUMENTS

| | | | |
|---|---|---|---|
| 2010/0030293 A1* | 2/2010 | Sarkar | A61B 5/08 607/18 |
| 2010/0241182 A1* | 9/2010 | Whitman | A61B 5/0464 607/5 |
| 2015/0342466 A1* | 12/2015 | Thakur | A61N 1/3624 600/484 |
| 2016/0045125 A1 | 2/2016 | Krueger et al. | |
| 2017/0238833 A1* | 8/2017 | Felix | A61B 5/02055 |
| 2017/0273589 A1* | 9/2017 | Sarkar | A61B 5/04325 |
| 2018/0104502 A1 | 4/2018 | Perschbacher et al. | |
| 2018/0192902 A1 | 7/2018 | Perschbacher et al. | |

FOREIGN PATENT DOCUMENTS

| | | |
|---|---|---|
| WO | WO-2016133799 A1 | 8/2016 |
| WO | WO-2019217052 A1 | 11/2019 |

OTHER PUBLICATIONS

"International Application Serial No. PCT/US2019/028113, International Search Report dated Jun. 13, 2019", 5 pgs.

"International Application Serial No. PCT/US2019/028113, Written Opinion dated Jun. 13, 2019", 5 pgs.

* cited by examiner

SYSTEMS AND METHODS FOR DETECTING ARRHYTHMIAS

CLAIM OF PRIORITY

This application claims the benefit of priority under 35 U.S.C. § 119(e) of U.S. Provisional Patent Application Ser. No. 62/668,392, filed on May 8, 2018, which is herein incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmias, such as atrial tachyarrhythmia. One type of atrial tachyarrhythmia is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself. Persistent AF may last for over a week and typically requires medication or other treatment to revert to normal sinus rhythm. AF is permanent if a normal heart rhythm cannot be restored with treatment. AF may be associated with stroke and requires anticoagulation therapy.

Another type of atrial tachyarrhythmia is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AF. Prolonged fast AFL may lead to decompensation with loss of normal heart function. This may manifest as effort intolerance, nocturnal breathlessness, or swelling of the legs or abdomen.

Timely detection of atrial tachyarrhythmia, such as AF or AFL, may be clinically important for assessing cardiac function. Some atrial tachyarrhythmia may be characterized by slow and stable ventricular rates. Such atrial tachyarrhythmic episodes may be mistakenly recognized by an IMD as a sinus rhythm, and are undetected or under-detected in some patients. This may adversely impact patient outcome.

Overview

Atrial tachyarrhythmia such as AF or AFL are characterized by fast atrial rate. In some patients, direct sensing of atrial activation rate with an electrode positioned in or near the atrium is not available or not feasible, such as patients not indicated for atrial lead implantation. A medical device, such as a single-chamber IMD with no dedicated atrial sensing/pacing lead, may detect the atrial tachyarrhythmia based on ventricular heart rate, without direct sensing of atrial activity. However, confounding factors such as noise, motion artifacts, or cardiac rhythms other than the atrial tachyarrhythmia may be mistakenly detected as atrial tachyarrhythmia events. For example, during AFL, impulses from the atria are conducted to the ventricles through the atrio-ventricular node (AV node). Due primarily to its longer refractory period, the AV node may exert a protective effect on heart rate at the ventricle by blocking atrial impulses in excess of approximately 180 beats per minute (bpm). If an AFL rate is 300 bpm, a two-to-one (2:1) heart block may develop such that only half of the atrial impulses can be conducted to the ventricle, resulting in a ventricular rate of 150 bpm. As the heart rate is a measure of the ventricular rather than atrial activity, a medical device that detects atrial tachyarrhythmia based on ventricular heart rate and not on atrial activity may be confounded by physiologic sinus rhythm at an elevated rate such as during tolerable physical activities (e.g., sinus tachycardia).

Arrhythmia can be detected using a comparison of a signal metric generated from a physiologic signal to a detection criterion, such as a detection threshold. Conventionally, the detection threshold is determined based on population data. A user (e.g., a healthcare provider) may manually adjust the population-based detection threshold for an individual patient. The population-based threshold, which is generally tuned to achieve a desired overall algorithm performance (e.g., sensitivity, specificity, or positive or negative predictive values), nevertheless may not provide optimal arrhythmia detection performance for one or some patients. Although manual programming of detection threshold may improve detection performance in some patients, it nevertheless lacks automaticity and generally consumes additional time and more medical resources for patient monitoring. Additionally, manual tuning of detection threshold may not be feasible for ambulatory patient management, in which case no proper medical personnel and resources may be readily available, or such an availability can be substantially delayed. As a result, arrhythmias such as AF or AFL may be undetected or falsely detected as sinus rhythm or other arrhythmic events. Inappropriate detection of an atrial tachyarrhythmia episode may decrease detection specificity, and result in lack of treatment or untimely treatment, or unnecessary or inappropriate therapies. False alerts to clinicians of the inappropriately detected arrhythmia, or presenting to clinicians a large volume of inappropriately detected arrhythmic events for review or adjudication, may adversely affect the device efficacy and unwarrantedly increase the healthcare cost associated with patient management. Consequently, this may diminish the clinical utility of the heart rate-based atrial tachyarrhythmia detection.

For at least foregoing reasons, the present inventors have recognized an unmet need for improved ambulatory arrhythmia detection system and methods, which can automatically adjust the device setting for an individual patient to more accurately detect arrhythmia like atrial tachyarrhythmia. This document discusses, among other things, systems, devices, and methods for detecting cardiac arrhythmias, such as an atrial tachyarrhythmia. An embodiment of arrhythmia detection system may include a detection criterion circuit that determines a patient-specific detection criterion using a baseline cardiac characteristic when the patient is free of cardiac arrhythmias. In an example, the detection criterion circuit may generate a patient-specific threshold of a signal metric by adjusting a population-based threshold of the signal metric, where the manner and the amount of adjustment is based on the patient baseline cardiac characteristic. The arrhythmia detection system may detect an arrhythmia episode using a physiologic signal sensed from the patient and the patient-specific arrhythmia detection threshold.

Example 1 is a system for detecting cardiac arrhythmia in a patient. The system comprises a detection criterion circuit and an arrhythmia detector circuit. The detection criterion circuit is configured to determine a baseline cardiac characteristic using a first physiologic signal sensed from the patient when the patient is free of cardiac arrhythmia, and determine a patient-specific arrhythmia detection threshold using the determined baseline cardiac characteristic. The arrhythmia detector circuit is configured to detect an arrhythmia episode using a second physiologic signal sensed from the patient and the patient-specific arrhythmia detection threshold.

In Example 2, the subject matter of Example 1 optionally includes the detection criterion circuit that may be further configured to determine a patient-specific arrhythmia confirmation threshold using the determined baseline cardiac characteristic. The arrhythmia detector circuit may be configured to confirm or reject the detected arrhythmia episode using the patient-specific arrhythmia confirmation threshold; wherein the patient-specific arrhythmia confirmation threshold corresponds to a higher specificity for detecting the cardiac arrhythmia than the arrhythmia detection threshold.

In Example 3, the subject matter of Example 2 optionally includes the arrhythmia detector circuit that may be configured to generate a first signal metric and a second signal metric different from the first signal metric respectively from the second physiologic signal, detect the arrhythmia episode by comparing the first signal metric to the patient-specific arrhythmia detection threshold, and confirm or reject the detected arrhythmia episode by comparing the second signal metric to the patient-specific arrhythmia confirmation threshold.

In Example 4, the subject matter of any one or more of Examples 1-3 optionally includes the detection criterion circuit that may be configured to detect a sinus rhythm in the patient using a third physiologic signal sensed from the patient, and determine the baseline cardiac characteristic during the detected sinus rhythm.

In Example 5, the subject matter of Example 4 optionally includes sensor circuitry configured to sense the first, second, and third physiologic signals.

In Example 6, the subject matter of Example 5 optionally includes the sensor circuitry coupled to a first sensor to sense the first physiologic signal and a second sensor to sense the second physiologic signal, the first sensor having a different type than the second sensor.

In Example 7, the subject matter of any one or more of Examples 4-6 optionally includes the detection criterion circuit that may be configured to detect the sinus rhythm using a population-based threshold.

In Example 8, the subject matter of any one or more of Examples 1-7 optionally includes the detection criterion circuit that may be configured to determine the patient-specific arrhythmia detection threshold by modifying a population-based threshold according to the baseline cardiac characteristic.

In Example 9, the subject matter of any one or more of Examples 1-8 optionally includes the detection criterion circuit that may be configured to update the baseline cardiac characteristic of the patient periodically or in response to a change in patient condition.

In Example 10, the subject matter of Example 9 optionally includes the detection criterion circuit that may be configured to update the baseline cardiac characteristic in response to a posture change.

In Example 11, the subject matter of any one or more of Examples 1-10 optionally includes the detection criterion circuit that may be configured to: determine the baseline cardiac characteristic during a training session with a training duration; evaluate a quality measure of the determined baseline cardiac characteristic; and adjust the training duration based on the quality measure of the baseline cardiac characteristic.

In Example 12, the subject matter of any one or more of Examples 1-11 optionally includes the arrhythmia detector circuit that may be configured to detect an atrial tachyarrhythmia episode using a patient-specific atrial tachyarrhythmia detection threshold.

In Example 13, the subject matter of Example 12 optionally includes the baseline cardiac characteristic that may include a ventricular rate variability metric during a sinus rhythm.

In Example 14, the subject matter of Example 12 optionally includes the baseline cardiac characteristic that may include an atrio-ventricular conduction block metric during a sinus rhythm.

In Example 15, the subject matter of any one or more of Examples 1-14 optionally includes the cardiac arrhythmia that may include a cardiac pause. The detection criterion circuit may be configured to determine a patient-specific R-wave amplitude threshold using the baseline cardiac characteristic, and the arrhythmia detector circuit may be configured to determine an R-wave amplitude metric from the second physiologic signal, and to detect a cardiac pause episode by comparing the R-wave amplitude metric to the patient-specific R-wave amplitude threshold.

Example 16 is a method of detecting cardiac arrhythmia in a patient using a medical system. The method comprises steps of sensing a first physiologic signal when the patient is free of cardiac arrhythmia and a second physiological signal different from the first physiologic signal using sensor circuitry; determining, via a detection criterion circuit, a baseline cardiac characteristic using the first physiologic signal; determining, via the detection criterion circuit, a patient-specific arrhythmia detection threshold using the determined baseline cardiac characteristic; and detecting, via an arrhythmia detector circuit, an arrhythmia episode using the second physiologic signal and the patient-specific arrhythmia detection threshold.

In Example 17, the subject matter of Example 16 optionally includes detecting an atrial tachyarrhythmia episode using a patient-specific atrial tachyarrhythmia detection threshold.

In Example 18, the subject matter of Example 17 optionally includes determining the baseline cardiac characteristic that may include generating, from the first physiologic signal during a sinus rhythm, signal metrics including one or more of: a ventricular rate variability metric; an atrioventricular conduction block metric; a signal morphology metric; or a signal quality metric.

In Example 19, the subject matter of Example 16 optionally includes steps of: determining a patient-specific arrhythmia confirmation threshold using the determined baseline cardiac characteristic; and confirming or rejecting the detected arrhythmia episode using the patient-specific arrhythmia confirmation threshold; wherein the patient-specific arrhythmia confirmation threshold corresponds to a higher specificity for detecting the cardiac arrhythmia than the arrhythmia detection threshold.

In Example 20, the subject matter of Example 16 optionally includes detecting a sinus rhythm in the patient using a third physiologic signal and a population-based threshold, and determining the baseline cardiac characteristic during the detected sinus rhythm.

In Example 21, the subject matter of Example 16 optionally includes determining the patient-specific arrhythmia detection threshold that may include modifying a population-based threshold according to the baseline cardiac characteristic.

In Example 22, the subject matter of Example 16 optionally includes updating the baseline cardiac characteristic of the patient periodically or in response to a change in patient condition.

In Example 23, the subject matter of any one or more of Examples 16-22 optionally includes steps of: determining the baseline cardiac characteristic during a training session with a training duration; evaluating a quality measure of the determined baseline cardiac characteristic; and adjusting the training duration based on the quality measure of the baseline cardiac characteristic.

The systems, devices, and methods discussed in this document may improve the medical technology of automated cardiac rhythm management (CRM) and prevention of worsening of cardiac function. The patient-specific detection criterion, such as a patient-specific detection threshold, as discussed in this document may enhance the performance and functionality of an implantable medical device. In certain examples, the patient-specific detection criterion takes into account the patient underlying medical condition, and improves sensitivity and specificity of detection of atrial tachyarrhythmia events, yet with little to no additional cost. The systems and methods discussed herein may reduce costs associated with false atrial tachyarrhythmia detections, or manual inspection required by such false determinations. In other examples, existing system performance can be maintained (e.g., high arrhythmia detection sensitivity and specificity, etc.) using lower cost or less obtrusive systems, apparatus, and methods. For example, because the system or device does not require direct sensing of atrial activity, the system complexity and implementation cost may be reduced. It may particularly be beneficial for patient not indicated for atrial lead implantation either for atrial activity sensing or for atrial pacing. Moreover, the arrhythmia detection discussed in this document may make more efficient use of device memory by storing information such as patient baseline cardiac characteristics, which are clinically relevant to atrial tachyarrhythmia detection. With improved atrial tachyarrhythmia detection, fewer alarms are provided, battery life can be extended, fewer unnecessary drugs and procedures may be scheduled, prescribed, or provided, and an overall system cost and power savings may be realized in contrast to existing medical devices and systems.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting cardiac arrhythmias. An embodiment of arrhythmia detection system may determine a patient-specific detection criterion using a baseline cardiac characteristic when the patient is free of cardiac arrhythmias. The patient-specific detection criterion may include a patient-specific arrhythmia detection threshold of a signal metric. The arrhythmia detection system may detect an arrhythmia episode using a physiologic signal sensed from the patient and the patient-specific arrhythmia detection threshold.

Figure 1:
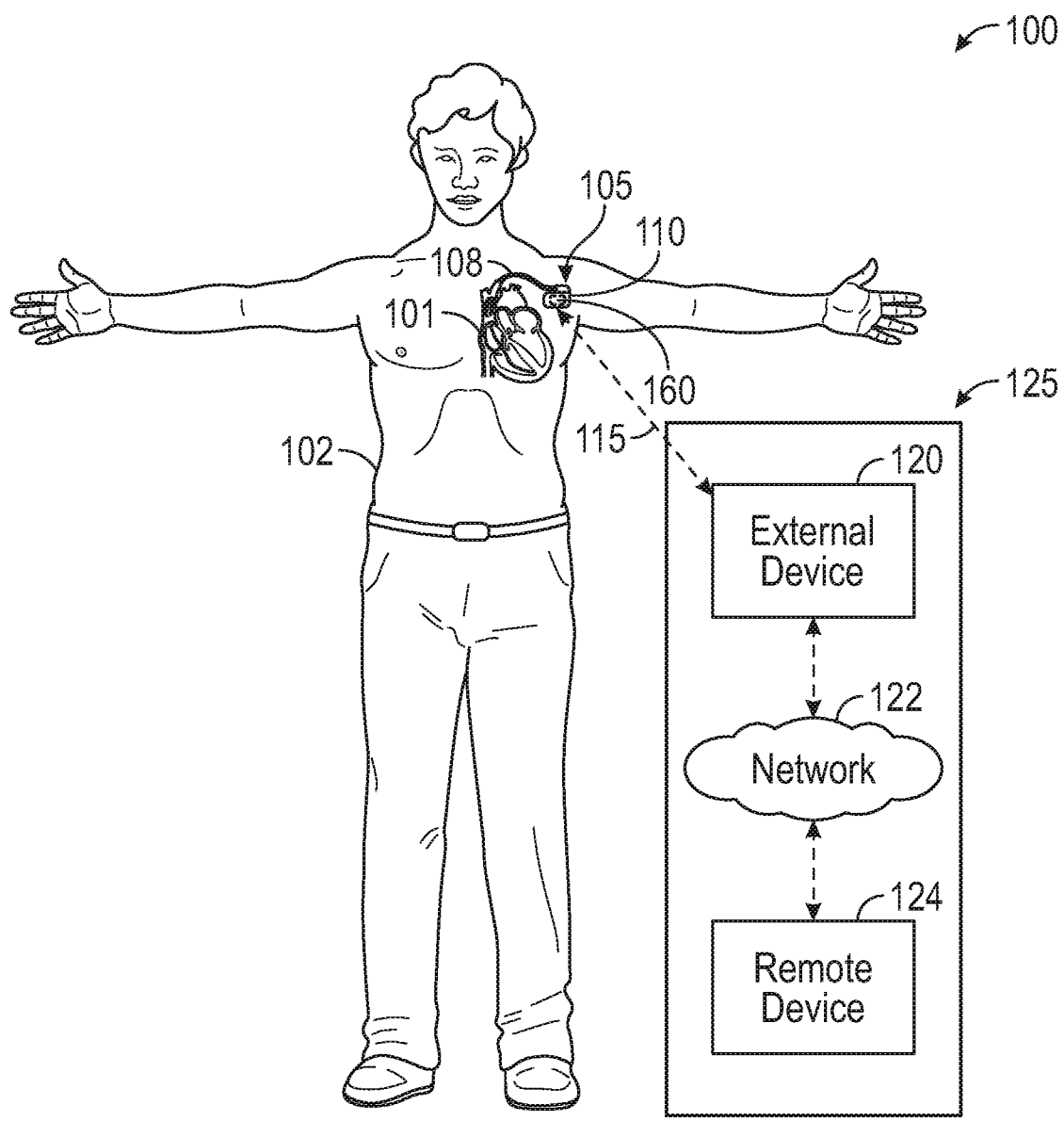
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMID 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a physiologic event detector circuit 160 configured to detect a physiologic event using the sensed physiologic signals. In an example, the physiologic event includes a cardiac arrhythmia episode, such as an episode of atrial fibrillation, atrial flutter, atrial tachycardia, supraventricular tachycardia, ventricular tachycardia, or ventricular fibrillation, cardiac pauses, among other brady- or tachy-arrhythmia. In an example, the physiologic event detector circuit 160 is configured to detect syncope, a presyncopal event or a precipitating event that may lead to a full-blown syncope. In some examples, the physiologic event detector circuit 160 is configured to detect worsening of a chronic medical condition, such as worsening heart failure (WHF). The physiologic event detector circuit 160 may execute a detection algorithm to monitor one or more physiologic signals continuously or periodically, and to detect the physiologic event automatically. Additionally or alternatively, the physiologic event detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a medical event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi"

interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event episodes, may be collected by the AMD 110, among other data acquisition sensors or devices associated with the patient 102. The remote device 124 may include a storage unit to store the patient data in a patient database. The storage unit may additionally store an association between a plurality of episode characterizations and a plurality of detection algorithms for detecting a medical event having respective episode characterizations. The server may process the device-generated event episodes to verify that a specific medical event (e.g., a cardiac arrhythmia type) is detected such that the device-detected event is a true positive (TP) detection; or that no such medical event is detected such that the device-detected event is a false positive (FP) detection. The processing of the device-generated medical event episodes may be based on a stored association. In an example, a first event episode may be presented to a user (e.g., a clinician), who would provide an adjudication decision and a first episode characterization. If the adjudication decision indicates that the first event episode is a FP detection, then the server may identify from the stored association a detection algorithm corresponding to the first episode characterization, and process a second event episode using at least the identified detection algorithm to determine that the second event episode is either a TP or a FP detection. The server may schedule a presentation of at least a portion of the second episode based on the processing result of the second episode. By using the detection algorithms tailored for recognizing episode with an episode characterization associated with a FP episode, more FP episodes having the same or similar episode characterization may be identified, and therefore avoided from being reviewed and adjudicated by the user. If the second event episode is determined to be a TP episode, then an alert is generated indicating further user review may be warranted.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a medical event prioritizer circuit configured to prioritize the alert notifications. For example, an alert of a detected medical event may be prioritized using a similarity metric between the physiologic data associated with the detected medical event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
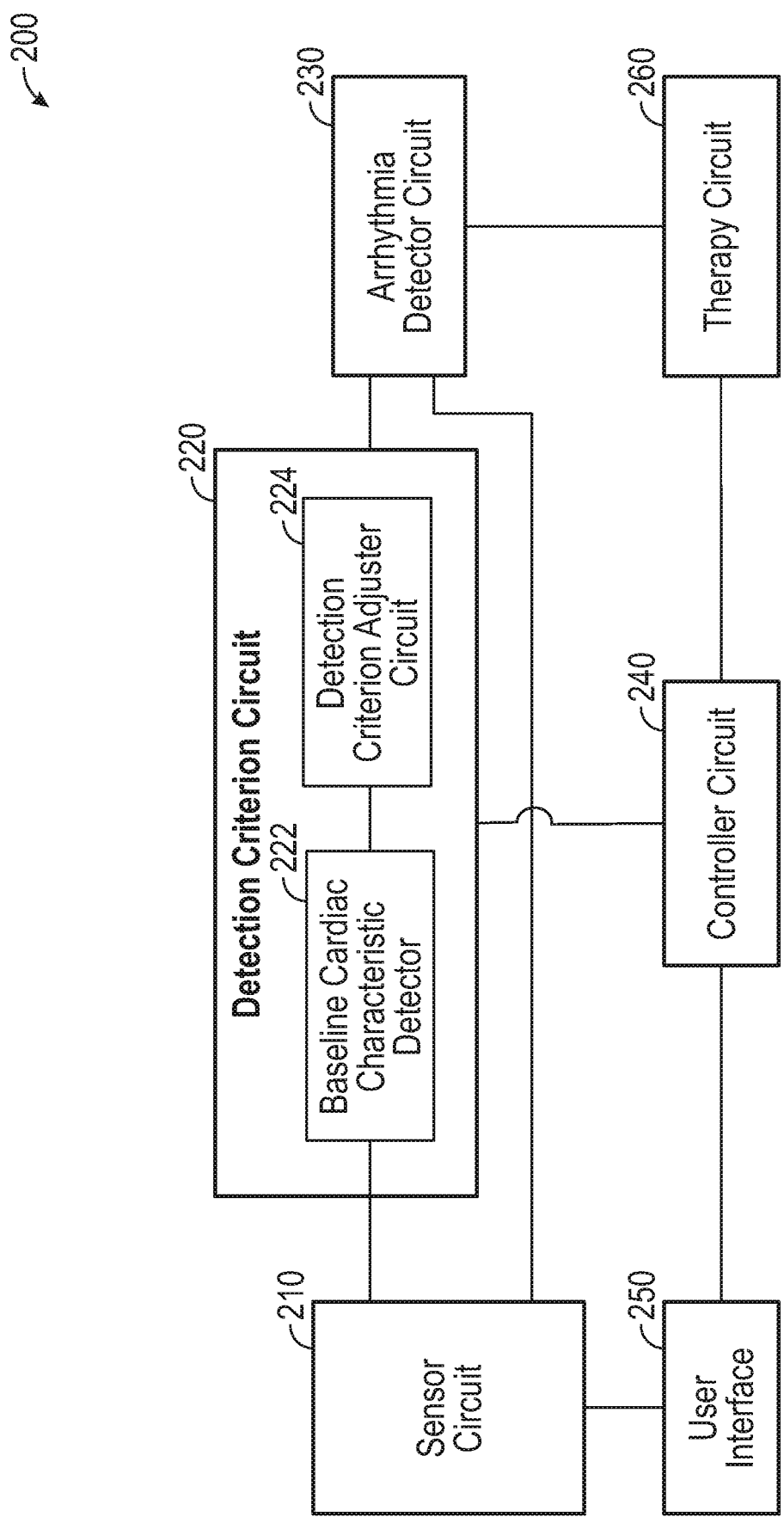
FIG. 2 illustrates generally an example of an arrhythmia detection system configured to detect an arrhythmia episode, such as atrial tachyarrhythmia episode.

FIG. 2 illustrates generally an example of an arrhythmia detection system 200 configured to detect an arrhythmia episode, such as an atrial tachyarrhythmia episode. Portions of the arrhythmia detection 200 may be included in the physiologic event detector circuit 160 of the AMD 110. The arrhythmia detection system 200 may include one or more of a sensor circuit 210, a detection criterion circuit 220, an arrhythmia detector circuit 230, a controller circuit 240, and a user interface unit 250. The arrhythmia detection system 200 may additionally include an optional therapy circuit 260.

The sensor circuit 210 may include a sense amplifier circuit to sense a physiologic signal from a patient via one or more implantable, wearable, or otherwise ambulatory sensors or electrodes associated with the patient. The sensed physiologic signal may contain information about pulsatile cardiac activity, such as heart rate or pulse rate. Examples of the physiologic signals may include surface electrocardiography (ECG) such as sensed from electrodes on the body surface, subcutaneous ECG such as sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiologic signal.

In some examples, the physiologic signals may be stored in a storage device such as an electronic medical record system. The sensor circuit 210 may retrieve a physiologic signal from the storage device in response to a command signal that is provided by a system user, or automatically generated in response to occurrence of a specific event.

The detection criterion circuit 220 may be coupled to the sensor circuit 210 to determine or adjust a detection criterion, such as a threshold value, for detecting a physiologic event such as a cardiac arrhythmia episode. The detection criterion circuit 220 may additionally determine or adjust a threshold for classifying an arrhythmia event into a particular arrhythmia type, such as classifying the detected atrial tachyarrhythmia episode as AF, AFL, or atrial tachycardia. The detection criterion may be determined or adjusted based on patient baseline characteristics to account for interpatient differences and intra-patient variation over time such as due to changing patient medical conditions. The resultant detection criterion may be a patient-specific criterion.

The detection criterion circuit 220 may include a baseline cardiac characteristic detector 222 and a detection criterion adjuster 224. The baseline cardiac characteristic detector 222 may determine patient baseline cardiac characteristic using a physiologic signal, such as sensed by the sensor circuit 210, when the patient is free of cardiac arrhythmias, such as in a sinus rhythm. In an example, the detection criterion circuit 220 may be coupled to a sinus rhythm detector to detect the sinus rhythm. In another example, sinus rhythm may be confirmed by a user such as a clinician. The baseline cardiac characteristic detector 222 may determine patient baseline cardiac characteristic during the sinus rhythm. Examples including the normal sinus rhythm detection for generating the baseline characteristic are discussed below, such as with reference to FIG. 3.

The baseline cardiac characteristic may be represented by a statistical or morphological signal feature of a physiologic signal acquired during the baseline (e.g., when the patient undergoes sinus rhythm). In an example of detecting atrial tachyarrhythmia such as an atrial fibrillation or atrial tachycardia episode, the baseline cardiac characteristic may include a baseline ventricular rate variability metric. Ventricular rates, or cardiac cycle lengths, may be detected using an electrophysiological signal, such as an ECG, a subcutaneous ECG, or an intracardiac EGM. Alternatively, ventricular rate may be detected using a mechano-physiological signal, such as a heart sound signal sensed using an accelerometer or a microphone sensor, cardiac or thoracic impedance signal, or a blood pressure signal, among other sensors. Ventricular rate variability, or cardiac cycle length variability, may be computed using a standard deviation, a variance, a range (e.g., a difference between minimum and maximum, an interquartile range between upper and lower quartiles, a difference between $10^{th}$ to $90^{th}$ percentiles or other ranges), or other measures of spreadness of a plurality of HR or CL measurements. The variability may be computed within a specified time period, such as a minute, a day, several days, or other specified time range.

In another example, the cardiac characteristics may include a ventricular rate pattern of consecutive decrease in ventricular rate. In an example, the ventricular rate pattern includes a pair of consecutive ventricular rate changes. Both ventricular rate changes are negative, referred to as a "double decrement" ventricular rate pattern. A double-decrement ratio, which represents a prevalence of the double decrement ventricular rate pattern over a specified time period or over a plurality of ventricular beats, may be computed, and used to detect atrial fibrillation or to differentiate between AF and ectopic beats. The baseline cardiac characteristic detector 222 may determine a baseline count of double-decrement beat pattern, or a baseline double-decrement ratio. Such a baseline double-decrement pattern of ventricular rate may distinguish frequent premature ventricular contractions (PVCs) from an AF episode, as PVCs alone typically do not produce double decrement patterns in ventricular rate. Krueger et al. U.S. patent application Ser. No. 14/825,669, entitled "ATRIAL FIBRILLATION DETECTION USING VENTRICULAR RATE VARIABILITY," refers to double decrement pattern in ventricular heart rate and its use in atrial arrhythmia detection, the disclosure of which is incorporated by reference herein in its entirety.

In yet another example, the cardiac characteristics may include a ventricular rate cluster, represented by a statistical distribution or a histogram of ventricular heart rates or cardiac cycle lengths. The ventricular rate cluster indicates regularity of ventricular rates of cardiac cycle lengths. Patients with AF are typically presented with irregular ventricular contractions. However, premature atrial contractions (PACs) may occur at irregular intervals. When PACs conduct to the ventricle, they may produce irregular ventricular rates, resulting in different ventricular clusters than AF. As such, the ventricular rate clusters may be used to distinguish frequent PACs from an AF episode. Perschbacher et al. U.S. patent application Ser. No. 15/864,953 entitled "ATRIAL FIBRILLATION DISCRIMINATION USING HEART RATE CLUSTERING," refers to histogram clusters of ventricular rates and their use in discriminating between AF and non-AF events, the disclosure of which is incorporated by reference herein in its entirety.

Additionally or alternatively, the baseline cardiac characteristics may include a metric representing the occurrence of various beat patterns of the cycle lengths or heart rates. For example, the beat pattern may include a number or percentage of consecutive heart beats during a 2-minute window that are within +/−5 beats per minute. In an example, the baseline cardiac characteristics may include an atrio-ventricular conduction block metric indicating a presence or degree of conduction abnormality during a sinus rhythm, such as Wenckebach score representing the prevalence of Wenckebach block over a time period. Examples of the Wenckebach detector may be based on a repetitiveness indictor of various beat patterns of the cycle lengths or heart rates, such as discussed in Perschbacher et al. U.S. patent application Ser. No. 15/786,824 entitled "SYSTEMS AND METHODS FOR ARRHYTHMIA DETECTION," the disclosure of which is incorporated by reference herein in its entirety. Additionally, the baseline cardiac characteristics may include a signal morphology metric representing regularity of ventricular depolarization signal morphology during sinus rhythm, or a signal quality metric such as a signal-to-noise (SNR). The signal quality or signal morphology indicator may differentiate the AF from noise.

In various examples, the baseline cardiac characteristic detector 222 may determine the baseline cardiac characteristic during a training session with a training duration. The training period may be different for various signal metrics representing different cardiac characteristics. In an example, the training duration may be based on the amount of data collected or a user-specified priority of a signal metric used by the arrhythmia detector circuit 230 to detect the arrhythmia event. In another example, the training duration may be based on a quality measure of the determined baseline cardiac characteristic (e.g., variability of the measures during the training period). For example, if the training period is nominally set to 30 days but a large amount of variability in patient baseline characteristics is observed during that timeframe, the baseline cardiac characteristic detector 222 may adjust the training period such as by extending the training duration to gather more data to establish the baseline characteristics. Such a training period adjustment allows for more reliable baseline characterization before generating a patient-specific detection threshold.

The detection criterion adjuster 224 may determine a patient-specific arrhythmia detection criterion, or adjust an existing arrhythmia detection criterion, based at least on the patient baseline characteristics, such as generated by the baseline cardiac characteristic detector 222. In an example, the patient-specific arrhythmia detection criterion includes a patient-specific detection threshold ($X_{TH}$) of a cardiac characteristic. The patient-specific threshold $X_{TH}$ may be computed using a function of the patient baseline cardiac characteristic. In an example, an association between various baseline cardiac characteristics and the corresponding detection threshold may be created and stored in a memory. The association may be implemented using a lookup table, an association map, or other data structures.

In an example, the patient-specific threshold $X_{TH}$ may be automatically set to an offset ($\Delta$) relative to a baseline signal metric value ($X_{BL}$) indicative of patient baseline cardiac characteristic, such as according to Equation (1) below:

$$X_{TH}=X_{BL}-\Delta \quad (1)$$

For example, in detecting an atrial tachyarrhythmia using a cardiac characteristic of ventricular rate cluster or ventricular rate or CL variability, the detection criterion adjuster 224 may set the patient-specific threshold ($VR_{TH}$) to be the patient baseline ventricular rate cluster or ventricular rate or CL variability ($VR_{BL}$) less a specified margin $\Delta$. For a patient with a high baseline ventricular rate variability, a lower patient-specific ventricular rate variability threshold corresponds to a higher sensitivity to detect an AF event in the patient. This may avoid or reduce the chance of missing an AF episode. In another example, an atrial tachyarrhythmia episode may be detected or confirmed using a Wenckebach score. The detection criterion adjuster 224 may set the patient-specific threshold for Wenckebach score ($WS_{TH}$) to be the patient baseline Wenckebach score ($WS_{BL}$) less a specified margin $\Delta$. As a high Wenckebach score indicates less likeliness of atrial fibrillation, a lower patient-specific Wenckebach score threshold corresponds to a higher specificity to detect an AF event. This may avoid or reduce false positive detections of AF episodes. In some examples, the detection criterion adjustor 224 may determine the patient-specific arrhythmia detection criterion by adjusting a population-based threshold, the detail of which is to be discussed below with reference to FIG. 3.

In various examples, the baseline cardiac characteristic detector 222 may evaluate and update one or more baseline characteristics periodically, triggered by a specific event such as a change in patient medical condition, or by a user command. In an example, the baseline characteristics may be updated in response to a patient posture change. In accordance with the update in baseline characteristics, the detection criterion adjustor 224 may automatically adjust the patient-specific detection criterion.

The arrhythmia detector circuit 230 may detect a cardiac arrhythmia using the patient-specific detection criterion. In an example, the cardiac arrhythmia includes an atrial tachyarrhythmia, such as atrial fibrillation (AF), atrial flutter (AFL), atrial tachycardia, or paroxysmal supraventricular tachycardia (PSVT), among others. The arrhythmia detector circuit 230 may generate a signal metric from a physiologic signal, such as an electrophysiological or mechano-physiological signal sensed by the sensor circuit 210, and detect the atrial tachyarrhythmia using a comparison between the signal metric and a patient-specific atrial tachyarrhythmia detection threshold. The signal metric represents a cardiac characteristic. In an example, an atrial tachyarrhythmia may be detected if the ventricular rate variability exceeds the patient-specific variability threshold $VR_{TH}$ by a specified margin. In another example, arrhythmia detector circuit 230 may detect atrial tachyarrhythmia based on signal morphology. An atrial tachyarrhythmia may be detected if a similarity measure between morphological features taken from the physiologic signal and a morphology template falls within a specified range relative to a patient-specific similarity threshold. The morphology template includes morphological features taken from patient baseline physiologic signal, such as sensed during a sinus rhythm. Examples of the similarity measure may include a correlation or be based on a distance in a signal feature space.

In various examples, detection criterion circuit 220 may additionally determine or adjust a patient-specific arrhythmia confirmation threshold ($X_{TH-C}$) using the baseline cardiac characteristic. The arrhythmia detector circuit 230 may detect an onset of cardiac arrhythmia using the patient-specific detection threshold $X_{TH}$, and further confirm or reject the detected cardiac arrhythmia using the patient-specific confirmation threshold $X_{TH-C}$. The confirmation threshold $X_{TH-C}$ may be different from the detection criterion $X_{TH}$, and corresponds to different sensitivity or specificity for detecting or confirming the cardiac arrhythmia. In an example, the confirmation threshold $X_{TH-C}$ may correspond to a higher specificity than the confirmation threshold $X_{TH-C}$, and the detection threshold $X_{TH}$ may correspond to a higher sensitivity than the confirmation threshold $X_{TH-C}$. In an example, the arrhythmia onset detection and confirmation may be both based on a measure of ventricular rate variability, and the detection criterion adjuster 224 may determine a patient-specific atrial tachyarrhythmia onset threshold to be $VR_{TH}=VR_{BL}-\Delta_1$, and a patient-specific atrial tachyarrhythmia confirmation threshold to be $VR_{TH-C} = VR_{BL} - \Delta_2$, where the offset $\Delta_2 < \Delta_1$ such that $VR_{TH-C} > VR_{TH}$. A higher confirmation threshold $VR_{TH-C}$ may correspond to a higher specificity, which may reduce false positive detections of atrial tachyarrhythmia episodes.

The arrhythmia detector circuit 230 may confirm the arrhythmia using the same physiologic signal or the same signal metric as that used for detecting arrhythmia onset (e.g., ventricular rate variability as exemplified above). Alternatively, a different type of physiologic signal or a different signal metric may be used to confirm the detection of the cardiac arrhythmia. By way of example and not limitation, the signal metrics representing cardiac characteristics for atrial tachyarrhythmia onset detection may include one or more of ventricular rate variability or CL variability, ventricular rate cluster or histogram features, or double decrement ventricular rate pattern. The signal metrics representing cardiac characteristics for atrial tachyarrhythmia confirmation may include one or more of morphological similarity, atrio-ventricular conduction block metric such as a Wenckebach score, or signal quality measure such as SNR.

As illustrated in FIG. 2, the detection criterion circuit 220 or the arrhythmia detector circuit 230 may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, the detection criterion circuit 220 and the arrhythmia detector circuit 230 may be implemented as a part of a microprocessor circuit. The microprocessor circuit may be a dedicated processor such as a digital signal processor, application specific integrated circuit (ASIC), microprocessor, or other type of processor for processing information including the physiologic signals received from the sensor circuit 210. Alternatively, the microprocessor circuit may be a general-purpose processor that may receive and execute a set of instructions of performing the functions, methods, or techniques described herein.

The controller circuit 240 controls the operations of the sensor circuit 210, the detection criterion circuit 220, the arrhythmia detector circuit 230, the user interface unit 250, and the data and instruction flow between these components. The user interface unit 250 may include an input device and an output device. In an example, at least a portion of the user interface unit 250 may be implemented in the external system 130. The input device may receive a user's programming input, such as parameters for adjusting detection criterion and parameters for detecting cardiac arrhythmia. The input device may include a keyboard, on-screen keyboard, mouse, trackball, touchpad, touch-screen, or other pointing or navigating devices. The input device may enable a system user to program the parameters used for sensing the physiologic signals, detecting the arrhythmias, and generating alerts, among others.

The output device may generate a human-perceptible presentation of the detected cardiac arrhythmia. The output device may include a display for displaying the sensed physiologic signal, intermediate measurements or computations such as patient baseline cardiac characteristics and patient-specific detection criterion, among others. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 260 may be configured to deliver a therapy to the patient in response to the detected cardiac arrhythmia. Examples of the therapy may include electrostimulation therapy delivered to the heart, a nerve tissue, other target tissues, a cardioversion therapy, a defibrillation therapy, or drug therapy. In some examples, the therapy circuit 260 may modify an existing therapy, such as adjust a stimulation parameter or drug dosage.

Figure 3:
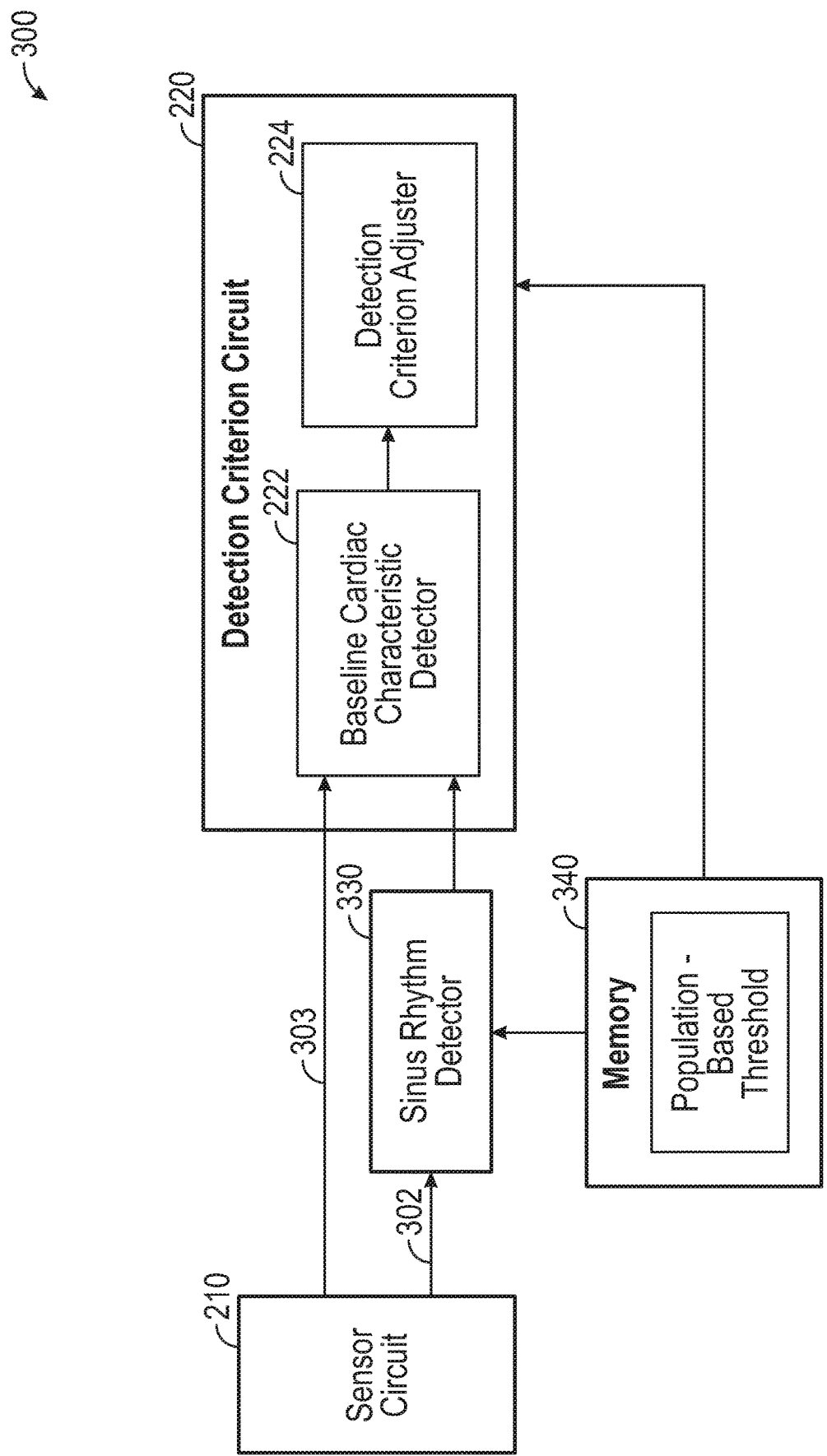
FIG. 3 illustrates generally an example of a system for adjusting arrhythmia detection criterion based on patient baseline cardiac characteristics.

FIG. 3 illustrates generally an example of a system 300 for adjusting arrhythmia detection criterion based on patient baseline cardiac characteristics. The system 300 represents an embodiment of at least a portion of the arrhythmia detection system 200, and includes the sensor circuit 210 and the detection criterion circuit 220, as discussed above in reference to FIG. 2. The system 300 may additionally include a sinus rhythm detector 330 configured to detect a sinus rhythm using a physiologic signal 302 sensed from the patient by the sensor circuit 210. In an example, the sinus rhythm detector 330 may generate from the signal 302 a signal metric (X) representing a cardiac characteristic, and detect the sinus rhythm using a comparison of the signal metric to a population-based arrhythmia detection threshold $(X_{TH\_P})$ stored in a memory circuit 340. The population-based threshold $X_{TH\_P}$ may be determined based on arrhythmia episodes from a patient cohort, such as patients at risk of cardiac arrhythmias.

In response to the detected sinus rhythm, the baseline cardiac characteristic detector 222 may determine patient baseline cardiac characteristic using a physiologic signal 303, which can be the same type as the signal 302 for detecting sinus rhythm. Alternatively, the physiologic signal 303 may be a different type of physiologic signal than the physiologic signal 302. The baseline cardiac characteristic detector 222 may determine from the physiologic signal 303 a baseline cardiac characteristic. The baseline cardiac characteristic may be a different type than the signal metric used for detecting sinus rhythm. For example, the sinus rhythm detector 330 may detect the sinus rhythm if a morphological similarity to a pre-determined morphology template exceeds a population-based threshold, and the baseline cardiac characteristic detector 222 may determine a baseline ventricular rate variability during the detected sinus rhythm.

Alternatively, the baseline cardiac characteristic may be the same type as the signal metric used for detecting sinus rhythm. In such a case, the population-based threshold, which is associated with the same signal metric, may be used by the detection criterion adjuster 224 to determine a patient-specific detection criterion such as an arrhythmia detection threshold or an arrhythmia confirmation threshold. In an example, the detection criterion adjuster 224 may determine the patient-specific arrhythmia detection threshold ($X_{TH}$) by adjusting the population-based threshold $X_{TH\_P}$, such as according to Equation (2) below:

$$X_{TH}=X_{TH\_P}+\delta \qquad (2)$$

The amount of adjustment $\delta$ may be based on the baseline cardiac characteristic. In an example where the signal metric represents ventricular rate variability, the adjustment may be proportional to the baseline ventricular rate variability, such that a larger adjustment $\delta$ may be used if the patient has more variable baseline ventricular rate. If the patient baseline ventricular rate is stable, a smaller positive or a negative adjustment $\delta$ may be applied to the population-based threshold to generate the patient-specific detection threshold.

Figure 4A:
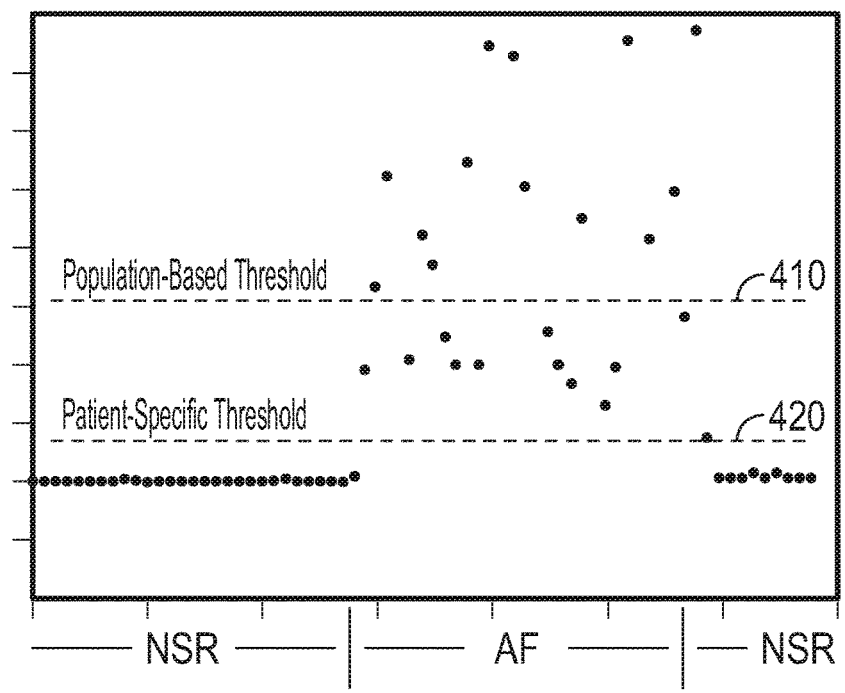
FIGS. 4A-4B are graphs illustrating examples of patient-specific atrial fibrillation detection threshold associated with signal metrics representing different cardiac characteristics.
Figure 4B:
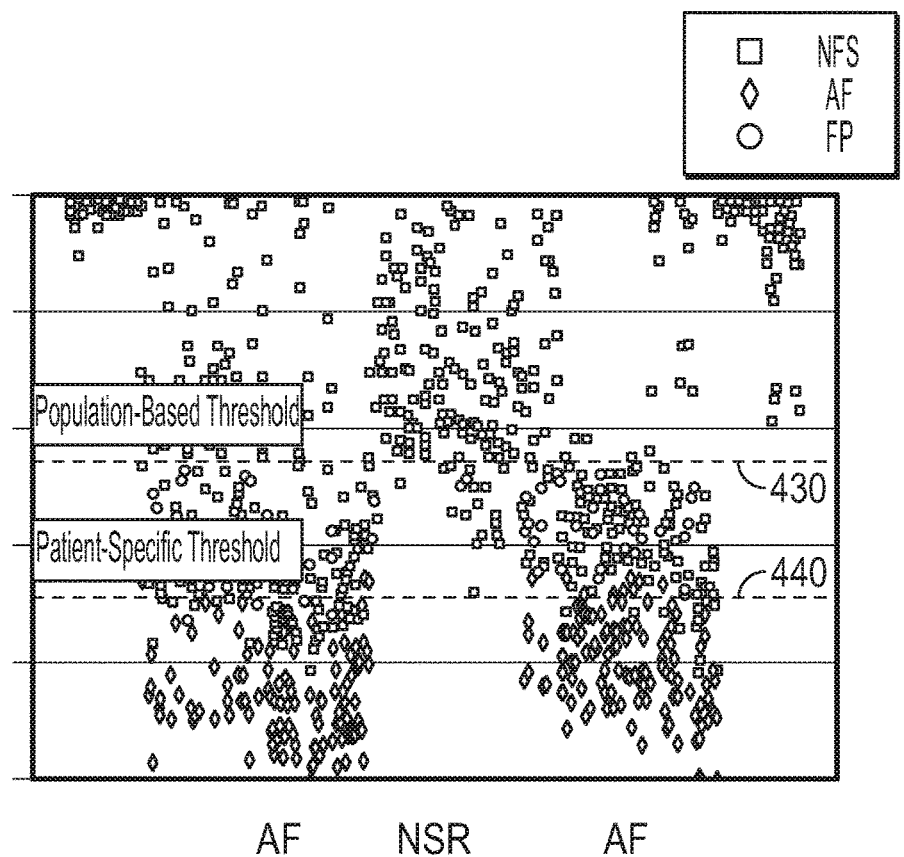

FIGS. 4A-4B are graphs illustrating examples of patient-specific atrial fibrillation (AF) detection threshold associated with signal metrics representing different cardiac characteristics. The patient-specific AF threshold may be determined using the system 300, which may modify a population-based threshold using information of patient baseline cardiac characteristics, as discussed above. In particular, FIG. 4A illustrates a trend of ventricular rate scatter indices over time in a subject. The ventricular rate scatter index represents a quantitative measure of variability of ventricular rates or cardiac cycle lengths. A smaller scatter index value indicates more stable ventricular rates, and less likely an AF episode is present. As illustrated in FIG. 4A, the sinus rhythm detector 330 may detect a sinus rhythm ("NSR") using a population-based threshold 410. The detection criterion circuit 224 may generate a patient-specific detection threshold 420, such as by modifying the population-based threshold 410 according to Equation (2) above. As the ventricular rate scatter indices are consistently below the population-based threshold 410, a negative adjustment $\delta$ may be used, such that the patient-specific detection threshold 420 is lower than the population-based threshold 410. The lower patient-specific AF detection threshold corresponds to a higher sensitivity to detect AF. The patient-specific detection threshold 420 may improve AF detection by reducing false negative detections (corresponding to events falling between the thresholds 410 and 420) that would have otherwise resulted had a population-based threshold 410 been used.

FIG. 4B illustrates a trend of Wenckebach scores over time in a subject. The Wenckebach score represents a quantitative measure of rhythmic patterns or stable rhythms. A higher Wenckebach score indicates a higher likelihood of rhythmic patterns, such that an ongoing AF episode is less likely. The detection criterion circuit 224 may generate a patient-specific AF confirmation threshold 440 by modifying the population-based threshold 430 according to Equation (2) above. As illustrated in FIG. 4B, the Wenckebach scores during sinus rhythm varied and close to the population-based threshold 410. A negative adjustment $\delta$ may be used, such that the patient-specific AF confirmation threshold 440 is lower than the population-based threshold 430. The lower patient-specific AF confirmation threshold corresponds to a higher specificity to detect AF. The patient-specific detection threshold 440 may reduce false positive detections (corresponding to events falling between the thresholds 430 and 440) that would otherwise have resulted had a population-based threshold 430 been used.

Figure 5:
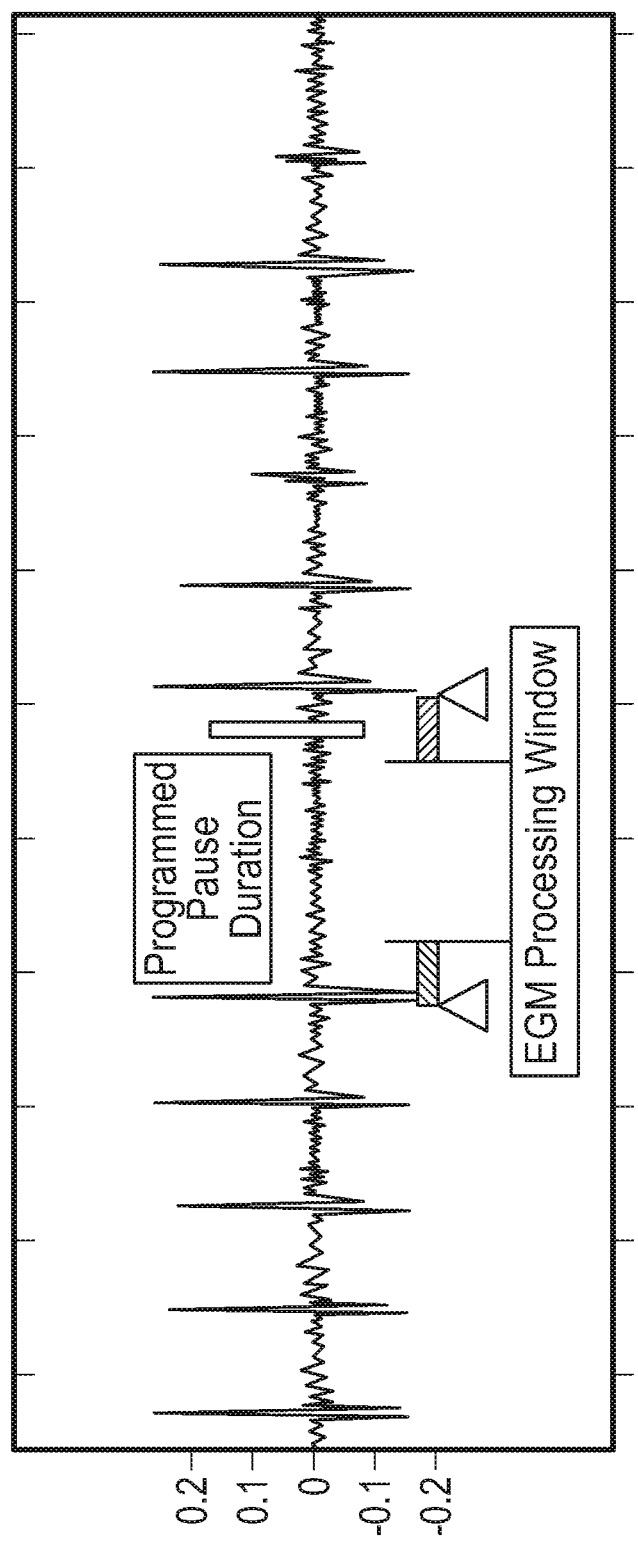
FIG. 5 is a graph illustrating an example of detecting cardiac pause using a trend of R-wave amplitude and a patient-specific threshold.

FIG. 5 is a graph illustrating an example of detecting cardiac pause using a trend of R-wave amplitude such as measured from an ECG or an EGM sensed by the sensing circuit 210, and a patient-specific threshold. Cardiac pause refers to an absence of electrical activity in the heart for an extended period of time. This may be attributed to sinus arrest, a condition where the sinoatrial node of the heart transiently ceases to generate the electrical impulses that normally stimulate the myocardial tissues to contract and thus the heart to beat. Sinus pause may cause severe lightheadedness, dizziness, near syncope, or a syncopal or passing-out episode. The arrhythmia detection system 200 may be configured to detect cardiac pause by comparing the R-wave amplitude to an amplitude threshold. In an example, a patient-specific R-wave amplitude threshold may be established using the system 300, which may modify a population-based R-wave amplitude threshold using information about patient baseline R-wave amplitudes during sinus rhythm.

In an example, the baseline cardiac characteristic detector 222 may determine a signal metric, such as a change of R-wave amplitude over time (AR). By way of example and not limitation, the temporal change of R-wave amplitude may be computed as a difference or a ratio between a central tendency of a plurality of R-waves within a first time window (e.g., three consecutive R waves) and a central tendency of a plurality of R-waves within a second time window prior to the first time window (e.g., three consecutive R waves immediately preceding the first three consecutive R waves in time). As illustrated in FIG. 5, a cardiac pause may lead to a decrease in the central tendency of R wave amplitude, and a termination of pause may lead to an increase in the central tendency of R wave amplitude. The detection criterion adjuster 224 may determine a patient-specific onset threshold ($\Delta R_{TH\_ON}$) for detecting onset of the cardiac pause, and optionally a patient-specific termination threshold ($\Delta R_{TH\_OFF}$) for detecting termination of the cardiac pause. Both the onset threshold ($\Delta R_{TH\_ON}$) and the termination threshold ($\Delta R_{TH\_OFF}$) may be determined by modifying the population-based threshold according to Equation (2) above. For example, if the patient has a larger baseline R wave amplitude, then a smaller adjustment $\delta$ may be applied such that the patient-specific threshold does not substantially differ from the population-based threshold. Conversely, if the patient has a smaller baseline R wave amplitude, then a negative adjustment $\delta$ may be applied such that the patient-specific threshold can be substantially smaller than the population-based threshold. This may improve the sensitivity of detecting cardiac pause for patients with lower than normal R wave amplitude.

Figure 6:
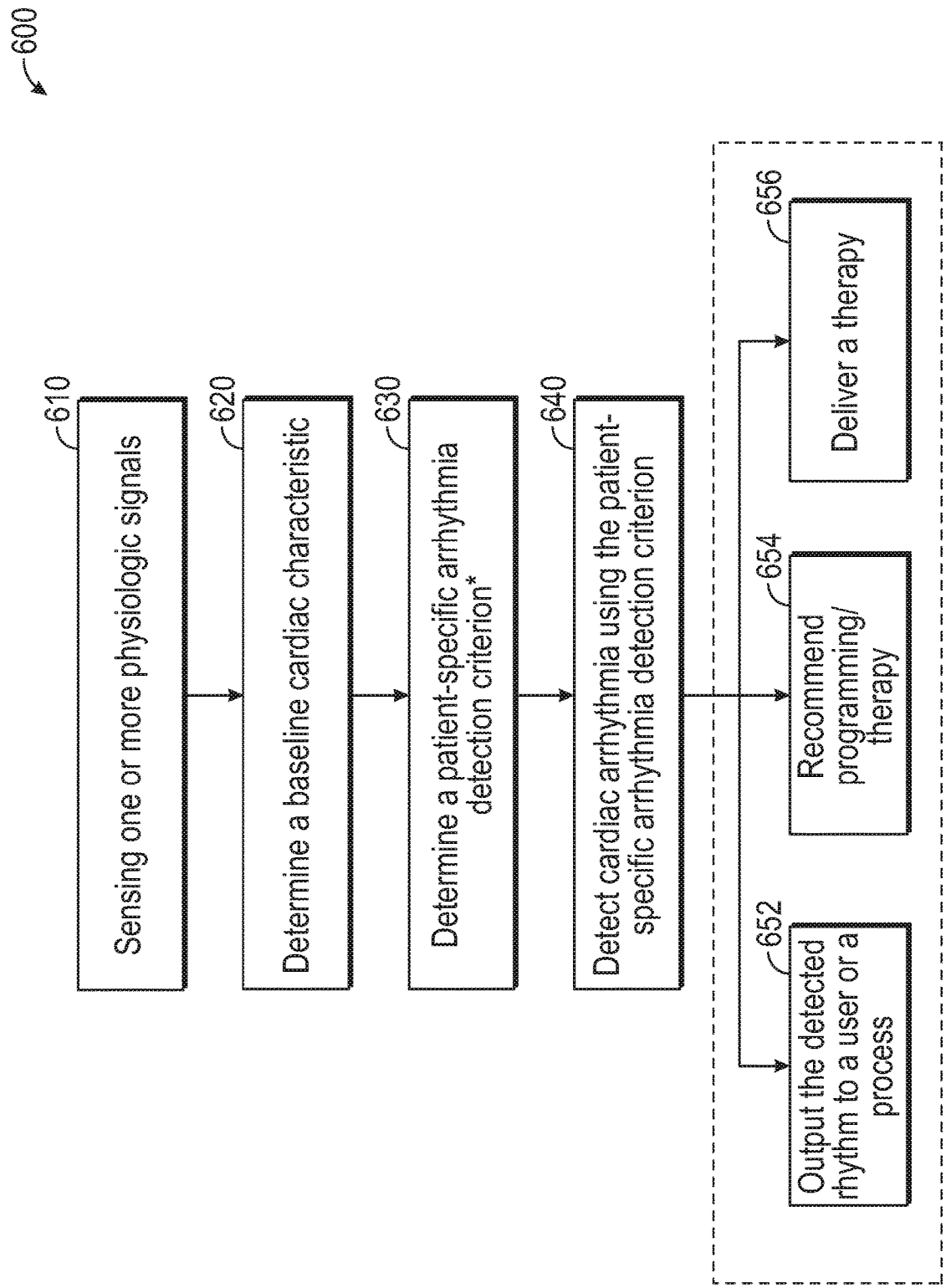
FIG. 6 is a flowchart illustrating an example of a method for detecting cardiac arrhythmia, such as an atrial tachyarrhythmia episode, using a patient-specific detection threshold.

FIG. 6 is a flowchart illustrating an example of a method 600 for detecting cardiac arrhythmia in a patient, such as atrial tachyarrhythmia episode. Examples of atrial tachyarrhythmia that can be detected using the method 600 may include atrial fibrillation (AF), atrial flutter (AFL), atrial tachycardia, paroxysmal supraventricular tachycardia (PSVT), among others. The method 600 may be implemented and executed in an ambulatory medical device such as an implantable or wearable device, or in a remote patient management system. In an example, the method 600 may be implemented in and executed by the cardiac arrhythmia detection circuit 160 in the AMD 110, the external system 130, or the arrhythmia detection system 200.

The method 600 commences at step 610, where one or more physiologic signals may be sensed from a subject.

Examples of the physiologic signals may include a cardiac electrical signal, such as ECG or EGM, or signals indicative of cardiac mechanical activity, such as pressure, impedance, heart sounds, or respiration signals. The sensed physiologic signal may be pre-processed, including amplification, digitization, filtering, or other signal conditioning operations. In some examples, patient physiologic signals may be sensed and stored in a storage device, such as an electronic medical record system, and retrieved for use such as according to the method 600.

At 620, a baseline cardiac characteristic may be determined using a physiologic signal sensed from the patient when the patient is free of cardiac arrhythmias such as during a sinus rhythm, such as automatically determined by the baseline cardiac characteristic detector 222. The baseline cardiac characteristic may include statistical or morphological signal metrics generated from the physiologic signal sensed during a sinus rhythm. In an example of detecting atrial tachyarrhythmia, the baseline cardiac characteristic may include a baseline ventricular rate or cardiac cycle length (CL) variability metric, a baseline ventricular rate pattern such as consecutive decrease in ventricular rate over at least two cardiac cycles (which is referred to as "double decrement" pattern), a baseline ventricular rate cluster or feature taken from a ventricular rate histogram, a quantitative measure of rhythmic patterns such as a Wenckebach score, a signal morphology metric representing regularity of ventricular depolarization, or a signal quality metric, among other metrics generated from the physiologic signal during a sinus rhythm.

At 630, a patient-specific arrhythmia detection criterion may be determined such using the determined baseline cardiac characteristic, such as by detection criterion adjuster 224. The patient-specific arrhythmia detection criterion includes a patient-specific arrhythmia detection threshold ($X_{TH}$) of a cardiac characteristic. The patient-specific threshold $X_{TH}$ may be computed using a function of the patient baseline cardiac characteristic, such as a signal metric value indicative of patient baseline cardiac characteristic less a specific offset, as represented by Equation (1) above. Alternatively, the patient-specific detection threshold $X_{TH}$ may be determined according to an association between various baseline cardiac characteristics and the corresponding detection threshold that is created and stored in a memory.

The patient-specific arrhythmia detection criterion may additionally include a patient-specific arrhythmia confirmation threshold of a cardiac characteristic. The confirmation threshold may be different from the detection criterion, and corresponds to a higher specificity than the confirmation threshold. The detection threshold may correspond to a higher sensitivity than the confirmation threshold. For example, the arrhythmia onset detection and confirmation may be both based on a measure of ventricular rate variability, the patient-specific atrial tachyarrhythmia confirmation threshold may be set to a higher level than the patient-specific atrial tachyarrhythmia detection threshold. This may help reducing false positive declarations of atrial tachyarrhythmia episodes, thus maintaining a higher specificity to the detected atrial tachyarrhythmia episodes.

At 640, a target cardiac arrhythmia, such as atrial tachyarrhythmia, may be detected using a physiologic signal sensed from the patient and the patient-specific arrhythmia detection criterion, such as by using the arrhythmia detector circuit 230. A signal metric may be generated from the physiologic signal, and an atrial tachyarrhythmia episode may be detected using a comparison between the signal metric and a patient-specific atrial tachyarrhythmia detection threshold. The physiologic signal used for detecting cardiac arrhythmia may be of a different type (e.g., sensed using a different physiologic sensor) than the physiologic signal used for establishing the baseline cardiac characteristics. In some examples, the step 640 further includes confirming or rejecting the detected cardiac arrhythmia using the patient-specific confirmation threshold. The confirmation may be based on the same physiologic signal or the same signal metric as that used for detecting arrhythmia onset. Alternatively, a different type of physiologic signal or a different signal metric may be used to confirm the detection of the cardiac arrhythmia.

The detected cardiac arrhythmia (optionally further confirmed arrhythmia) may be provided to one or more of the processes 652, 654, or 656. At 652, the cardiac arrhythmia may be output to a user or a process, such as via an output device of the user interface 250. In an example, the detected arrhythmic episode may be displayed on a display, including the sensed physiologic signal, patient baseline cardiac characteristics and patient-specific detection criterion, among others. Hard copies of the detection information may be generated. In various examples, alerts, alarms, emergency calls, or other forms of warnings may be generated to signal the system user about the detected arrhythmic episode.

At 654, a recommendation may be generated and provided to a user. The recommendation may include one or more of further diagnostic tests to be performed, antiarrhythmic therapy to treat the detected arrhythmia or to alleviate the arrhythmic complications. The recommendation may include adjustment of one or more arrhythmia detection parameters, such as the offset relative to patient baseline cardiac characteristics as provided in Equation (1). The method 600 may include the optional step 656 of delivering a therapy to the patient in response to the detected cardiac arrhythmia, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia.

Figure 7:
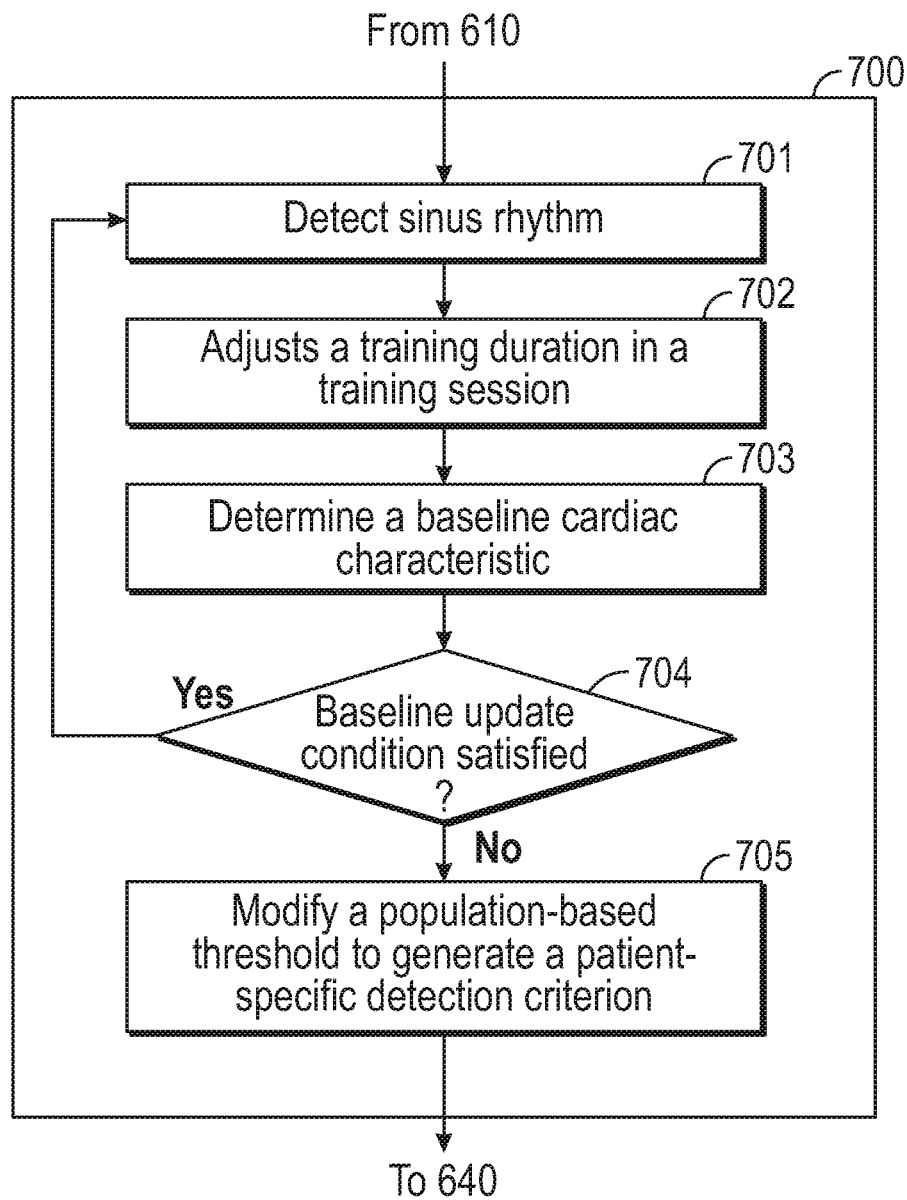
FIG. 7 is a flowchart illustrating an example of a method of determining a patient-specific criterion for detecting a cardiac arrhythmia.

FIG. 7 is a flowchart illustrating an example of a method 700 of determining a patient-specific criterion for detecting a cardiac arrhythmia. The method 700 represents an embodiment of a portion of the method 600, such as steps 620-630, and may be implemented in and executed by the system 300.

As illustrated in FIG. 7, a sinus rhythm may be detected at 701 using a physiologic signal sensed from the patient. A signal metric representing a cardiac characteristic may be generated from the sensed physiologic signal, and compared to a population-based arrhythmia detection threshold. The population-based threshold may be determined using arrhythmia episodes from a patient cohort, such as patients at risk of cardiac arrhythmias.

The baseline cardiac characteristic may be determined during a training session with a training duration. At 702, the training duration may be adjusted for the signal metric used to establish baseline cardiac characteristics. The training period may be different for various signal metrics. In an example, the training duration may be based on the amount of data collected or a user-specified priority of a signal metric. In another example, the training duration may be based on a quality measure of the determined baseline cardiac characteristic (e.g., variability of the measures during the training period). Such a training period adjustment allows for more reliable baseline characterization before generating a patient-specific detection threshold.

At 703, patient baseline cardiac characteristic may be determined in response to the detected sinus rhythm. The physiologic signal used for determining the baseline cardiac characteristics may be of the same type as the signal for detecting sinus rhythm. Alternatively, different types of physiologic signals, such as sensed by different physiologic sensors, may be used for determining the baseline cardiac characteristics or for detecting sinus rhythm.

One or more baseline characteristics may be updated to account for changes in patient conditions. At 704, baseline update condition is checked, such as to determine whether a baseline update is due according to a specified periodic update schedule, or whether an update triggering condition such as a change in patient medical condition, a change in posture or physical activity, has been satisfied. If the baseline update condition is satisfied, then baseline characteristics may be updated by re-detecting the sinus rhythm at 701; otherwise, at 705, the baseline cardiac characteristics may be used to modify a population-based threshold to generate a patient-specific arrhythmia detection threshold. The patient-specific arrhythmia detection threshold may be set to a value relative to the population-based threshold, such as according to Equation (2). In an example, the amount of adjustment may be based on the degree of variability of the baseline ventricular rate. For example, a larger adjustment may be used if the patient has more variable baseline ventricular rates. Also at 705, the baseline cardiac characteristics may also be used to modify a population-based threshold to generate a patient-specific arrhythmia confirmation threshold, such as according to Equation (2) above. The patient-specific arrhythmia detection criterion may be used to detect cardiac arrhythmia at 640.

Figure 8:
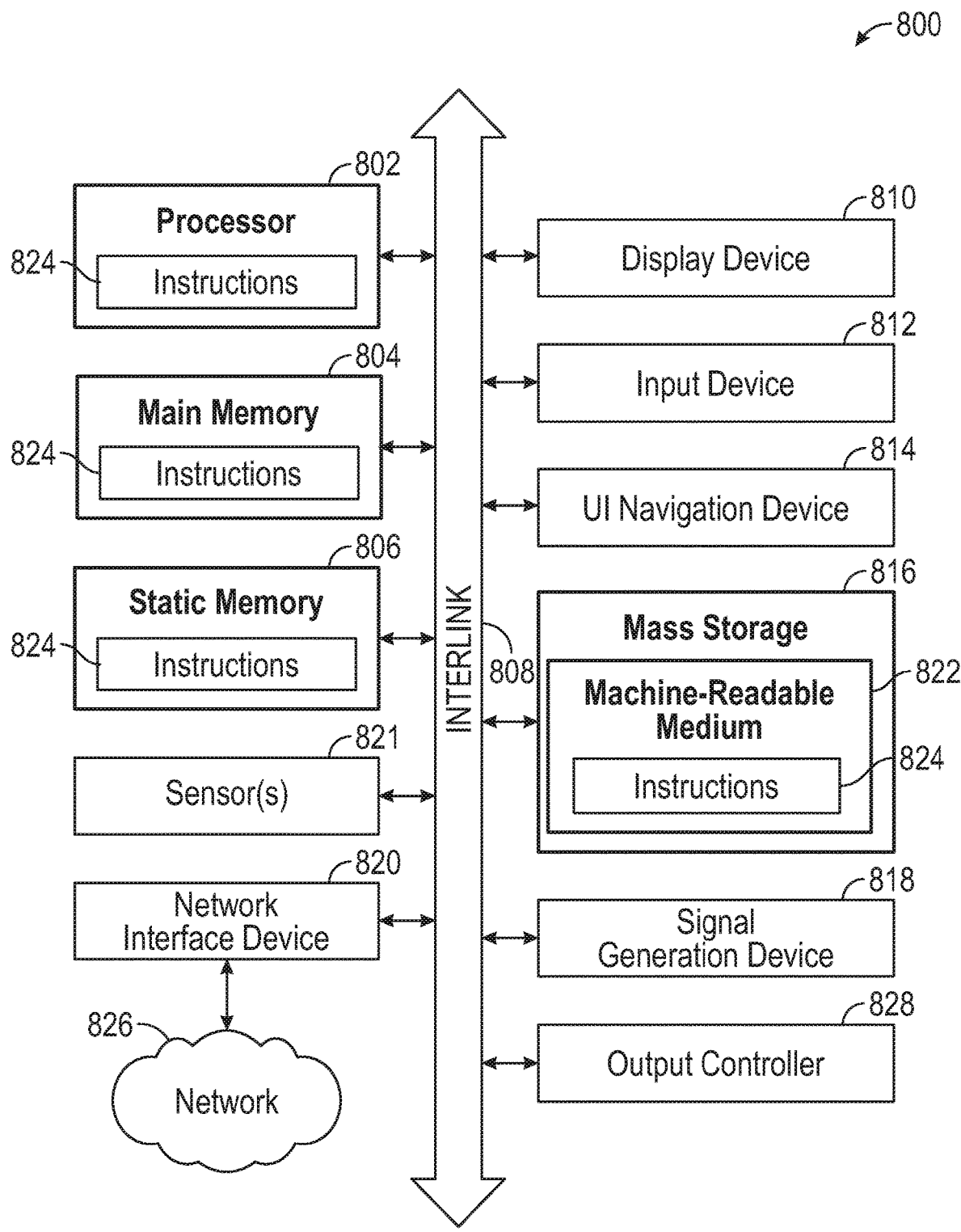
FIG. 8 illustrates generally a block diagram of an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine-readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802. 11 family of standards known as WiFi®, IEEE 802. 16 family of standards known as WiMax®), IEEE 802. 15. 4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for detecting atrial arrhythmia in a patient, comprising:
   a detection criterion circuit configured to:
      receive physiological information of the patient;
      detect a period of normal sinus rhythm in the patient using the received physiological information and a population-based threshold;
      determine a baseline cardiac characteristic using the received physiological information during the detected period of normal sinus rhythm; and
      determine a patient-specific arrhythmia detection threshold as an offset relative to the determined baseline cardiac characteristic; and
   an arrhythmia detector circuit configured to detect an atrial arrhythmia episode using the received physiological information and the patient-specific arrhythmia detection threshold.

2. The system of claim 1, wherein:
   the detection criterion circuit is further configured to determine a patient-specific arrhythmia confirmation threshold using the determined baseline cardiac characteristic; and
   the arrhythmia detector circuit is configured to confirm or reject the detected atrial arrhythmia episode using the patient-specific arrhythmia confirmation threshold;
   wherein the patient-specific arrhythmia confirmation threshold corresponds to a higher specificity for detecting the atrial arrhythmia than the arrhythmia detection threshold.

3. The system of claim 2, wherein the arrhythmia detector circuit is configured to:
   generate, from the received physiological information, a first signal metric and a second signal metric different from the first signal metric;
   detect the atrial arrhythmia episode by comparing the first signal metric to the patient-specific arrhythmia detection threshold; and
   confirm or reject the detected atrial arrhythmia episode by comparing the second signal metric to the patient-specific arrhythmia confirmation threshold.

4. The system of claim 1, wherein the detection criterion circuit is configured to detect the period of normal sinus rhythm in the patient using heart rates or morphologies of a cardiac signal sensed from the patient and the population-based threshold, and to determine the baseline cardiac characteristic using ventricular rate variability during the detected period of normal sinus rhythm.

5. The system of claim 1, wherein the detection criterion circuit is configured to determine the patient-specific arrhythmia detection threshold by modifying the population-based threshold according to the baseline cardiac characteristic.

6. The system of claim 1, wherein the detection criterion circuit is configured to update the baseline cardiac characteristic of the patient periodically or in response to a change in patient condition.

7. The system of claim 1, wherein the detection criterion circuit is configured to:
   determine the baseline cardiac characteristic during a training session with a training duration;
   evaluate a quality measure of the determined baseline cardiac characteristic; and
   adjust the training duration based on the quality measure of the baseline cardiac characteristic.

8. The system of claim 1, wherein the baseline cardiac characteristic includes a baseline ventricular rate variability metric during the detected period of normal sinus rhythm, and wherein the offset has a negative value such that the patient-specific arrhythmia detection threshold is lower than the baseline ventricular rate variability metric.

9. The system of claim 1, wherein the baseline cardiac characteristic includes a baseline atrio-ventricular conduction block metric during the detected period of normal sinus rhythm.

10. The system of claim 1, wherein:
the detection criterion circuit is configured to determine a patient-specific R-wave amplitude threshold using the baseline cardiac characteristic; and
the arrhythmia detector circuit is configured to determine an R-wave amplitude metric from thenal received physiological information, and to detect a cardiac pause episode by comparing the R-wave amplitude metric to the patient-specific R-wave amplitude threshold.

11. A method of detecting atrial arrhythmia in a patient using a medical system, the method comprising:
receiving physiological information of the patient;
detecting, via a detection criterion circuit, a period of normal sinus rhythm in the patient using the received physiological information and a population-based threshold;
determining, via the detection criterion circuit, a baseline cardiac characteristic using the received physiological information during the detected period of normal sinus rhythm;
determining, via the detection criterion circuit, a patient-specific arrhythmia detection threshold as an offset relative to the determined baseline cardiac characteristic; and
detecting, via an arrhythmia detector circuit, an atrial arrhythmia episode using the received physiological information and the patient-specific arrhythmia detection threshold.

12. The method of claim 11, wherein determining the baseline cardiac characteristic includes generating, from the received physiological information during the detected period of normal sinus rhythm, signal metrics including one or more of:
a ventricular rate variability metric;
an atrio-ventricular conduction block metric;
a signal morphology metric; or
a signal quality metric.

13. The method of claim 11, further comprising:
determining a patient-specific arrhythmia confirmation threshold using the determined baseline cardiac characteristic; and
confirming or rejecting the detected atrial arrhythmia episode using the patient-specific arrhythmia confirmation threshold;
wherein the patient-specific arrhythmia confirmation threshold corresponds to a higher specificity for detecting the atrial arrhythmia than the arrhythmia detection threshold.

14. The method of claim 11, wherein: detecting the period of normal sinus rhythm in the patient includes using morphologies of a cardiac signal and the population-based threshold; and determining the baseline cardiac characteristic includes using ventricular rate variability during the detected period of normal sinus rhythm.

15. The method of claim 11, wherein determining the patient-specific arrhythmia detection threshold includes modifying the population-based threshold according to the baseline cardiac characteristic.

16. The method of claim 11, further comprising updating the baseline cardiac characteristic of the patient periodically or in response to a change in patient condition.

17. The method of claim 11, further comprising:
determining the baseline cardiac characteristic during a training session with a training duration;
evaluating a quality measure of the determined baseline cardiac characteristic; and
adjusting the training duration based on the quality measure of the baseline cardiac characteristic.

18. The system of claim 8, wherein the offset is proportional to the baseline ventricular rate variability metric.

19. The system of claim 9, wherein the baseline atrio-ventricular conduction block metric includes a baseline Wenckebach block prevalence metric, and wherein the offset has a negative value such that the patient-specific arrhythmia detection threshold is lower than the baseline Wenckebach block prevalence metric.

20. A system for detecting atrial arrhythmia in a patient, comprising:
a detection criterion circuit configured to:
receive heart rates and heart rate variability sensed from the patient;
detect a period of normal sinus rhythm in the patient using the received heart rates and a population-based threshold;
determine a baseline heart rate variability using the received heart rate variability during the detected period of normal sinus rhythm; and
determine a patient-specific arrhythmia detection threshold as an offset relative to the determined baseline heart rate variability; and
an arrhythmia detector circuit configured to detect an atrial arrhythmia episode using the received heart rate variability and the patient-specific arrhythmia detection threshold.

* * * * *